US009157851B2

(12) United States Patent
Takebe et al.

(10) Patent No.: US 9,157,851 B2

(45) Date of Patent: Oct. 13, 2015

(54) DRUG EVALUATION METHOD AND DRUG EVALUATION DEVICE

(71) Applicant: HAMAMATSU PHOTONICS K.K., Hamamatsu-shi, Shizuoka (JP)

(72) Inventors: Gen Takebe, Hamamatsu (JP); Yoichi Kawada, Hamamatsu (JP); Kouichiro Akiyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 28 days.

(21) Appl. No.: 13/742,616

(22) Filed: Jan. 16, 2013

(65) Prior Publication Data

US 2013/0187050 A1 Jul. 25, 2013

(30) Foreign Application Priority Data

Jan. 25, 2012 (JP) ................................ 2012-013427

(51) Int. Cl.

*G01J 5/02* (2006.01)
*G01N 21/3577* (2014.01)
*G01N 21/3563* (2014.01)
*G01N 21/3586* (2014.01)

(52) U.S. Cl.

CPC ........ *G01N 21/3577* (2013.01); *G01N 21/3563* (2013.01); *G01N 21/3586* (2013.01)

(58) Field of Classification Search

CPC .................................................. G01N 21/3586
USPC .................. 250/339.01–339.12, 341.1–341.8
See application file for complete search history.

(56) References Cited

U.S. PATENT DOCUMENTS 7,812,959 B1 * 10/2010 Kim .............................. 356/458
2003/0175160 A1 9/2003 Archibald et al.

(Continued)

FOREIGN PATENT DOCUMENTS

| | | |
|---|---|---|
| EP | 2273254 | 1/2011 |
| JP | 2001508766 A | 7/2001 |
| JP | 2007-077000 A | 3/2007 |

(Continued)

OTHER PUBLICATIONS

Davies et al., "Terahertz spectroscopy of explosives and drugs," Mar. 2008, Materials Today, vol. 11, No. 3, pp. 18-26.*

(Continued)

*Primary Examiner* — Kiho Kim

(74) *Attorney, Agent, or Firm* — Drinker Biddle & Reath LLP

(57) ABSTRACT

The drug evaluation device obtains, by an attenuated reflection method using a terahertz wave, an evaluation absorption spectrum for a frequency with respect to a liquid to be evaluated. When crystalline particles are suspended in a liquid, an absorption peak having a peak area corresponding to the amount of suspension appears in its absorption spectrum. Therefore, whether or not and by what ratio crystalline particles are suspended in the liquid can be determined according to whether or not the absorption peak exists and the peak area. When amorphous particles are suspended in the liquid, the baseline of its absorption spectrum lowers according to the ratio of amorphous particles suspended in the liquid. Therefore, whether or not and by what ratio amorphous particles are suspended in the liquid can be determined according to the lowering amount of the baseline.

28 Claims, 7 Drawing Sheets

(56) References Cited

U.S. PATENT DOCUMENTS

| | | | | |
|---|---|---|---|---|
| 2006/0096522 | A1* | 5/2006 | Singh | 117/3 |
| 2007/0083143 | A1* | 4/2007 | Braig et al. | 604/6.08 |

FOREIGN PATENT DOCUMENTS

| | | |
|---|---|---|
| JP | 2007-198950 A | 8/2007 |
| JP | 2008-185552 A | 8/2008 |
| JP | 2008-304444 | 12/2008 |
| WO | WO-2012073561 | 6/2012 |
| WO | WO-2012128001 | 9/2012 |

OTHER PUBLICATIONS

Taday et al., "Using terahertz pulse spectroscopy to study the crystalline structure of a drug: a case study of the polymorphs of ranitidine hydrochloride," Apr. 2003, Journal of Pharmaceutical Sciences, vol. 92, No. 4, pp. 831-838.*

Tanabe et al., "Attenuated total relection spectroscopy of liquids using GaP-Raman Terahertz spectrometer," 2005, IEEE joint $30^{th}$ International Conference on Infrared and Millimeter Waves and 13th International Conference on Terahertxz Electronics, pp. 50-51.*

Vahur et al., "ATR-FT-IR spectroscopy in region of 550-230 cm-1 for identification of inorganic pigments," 2010, Spectrochimica Acta Part A, vol. 75, pp. 1061-1072.*

S. Vahur, et al., "ATR-FT-IR Spectroscopy in the Region of 500-230 $cm^{-1}$ for Identification of Inorganic Red Pigments," Spectrochimica Acta Part A: Molecular and Biomolecular Spectroscopy, 2009, pp. 1-8.

Clare J. Strachan et al., "Using terahertz pulsed spectroscopy to study crystallinity of pharmaceutical materials," Chemical Physics Letters, vol.390, May 21, 2004, pp. 20-24.

* cited by examiner

DRUG EVALUATION METHOD AND DRUG EVALUATION DEVICE

BACKGROUND OF THE INVENTION

1. Field of the Invention

The present invention relates to a drug evaluation method and a drug evaluation device.

2. Related Background Art

Known as an example of techniques in this kind of field is a method of manufacturing an iodinated organic X-ray contrast agent disclosed in Japanese Translated International Application Laid-Open No. 2001-508766. In the process of manufacturing the contrast agent, this conventional method monitors a reaction compound in a liquid by infrared spectroscopy and determines crystallinity of a reaction mixture according to multivariate analysis of calibration data obtained by the infrared spectroscopy.

SUMMARY OF THE INVENTION

Meanwhile, one of states of drugs in a liquid is suspension. The suspension indicates a state where a material is not dissolved but mixed as uniform particles in the liquid. Drugs may be suspended as crystalline or amorphous particles in liquids, and it may become necessary to determine such states when evaluating the drugs.

However, the above-mentioned method of Patent Literature 1 does not specifically disclose any multivariate analysis concerning the evaluation of drugs suspended in liquids. While techniques such as X-ray analysis and thermal analysis have been known as examples of conventional techniques of other crystal analyses, the former is intended for solids, while the latter is hard to perform measurement at the boiling point of its solvent or higher, which seem to make them unsuitable for evaluating drugs suspended in liquids.

For solving the problems mentioned above, it is an object of the present invention to provide a drug evaluation method and a drug evaluation device which make it possible to evaluate drugs suspended in liquids.

For achieving the above-mentioned object, the present invention provides a drug evaluation method for evaluating crystallinity of a drug suspended in a liquid, the method comprising obtaining by an attenuated reflection method using a terahertz wave an evaluation absorption spectrum for a frequency concerning the liquid to be evaluated and determining whether or not there is a crystalline particle suspended in the liquid according to whether or not an absorption peak exists in the evaluation absorption spectrum.

This drug evaluation method obtains, by an attenuated reflection method using a terahertz wave, an evaluation absorption spectrum for a frequency concerning a liquid to be evaluated. When a crystalline particle is suspended in a liquid, an absorption peak appears in its absorption spectrum. Therefore, whether or not there is a crystalline particle suspended in the liquid can be determined according to whether or not the absorption peak exists.

Preferably, the ratio of the crystalline particle suspended in the liquid is determined according to the area of the absorption peak in the evaluation absorption spectrum. When the crystalline particle is suspended in the liquid, the area of the absorption peak in its absorption spectrum increases and decreases depending on the ratio of the crystalline particle in the liquid. Therefore, the ratio of the crystalline particle in the liquid can be determined according to the area of the absorption peak.

Preferably, a reference absorption spectrum for a frequency concerning a liquid serving as a reference is obtained by an attenuated reflection method using a terahertz wave, and whether or not there is an amorphous particle suspended in the liquid is determined according to whether or not a baseline of the evaluation absorption spectrum changes from a baseline of the reference absorption spectrum. When an amorphous particle is suspended in a liquid, the baseline of its absorption spectrum differs from the baseline of the absorption spectrum of the reference liquid. Therefore, whether or not there is an amorphous particle suspended in the liquid can be determined according to whether or not the baseline changes.

Preferably, the ratio of the amorphous particle suspended in the liquid is determined according to the amount of change in the baseline of the evaluation absorption spectrum from the baseline of the reference absorption spectrum. When the amorphous particle is suspended in a liquid, the baseline of its absorption spectrum varies according to the ratio of the amorphous particle in the liquid. Therefore, the ratio of the amorphous particle in the liquid can be determined according to the amount of change in the baseline.

Preferably, a reference absorption spectrum for a frequency concerning a liquid serving as a reference is obtained by an attenuated reflection method using a terahertz wave, and whether or not there are crystalline and amorphous particles suspended in the liquid is determined according to whether or not a baseline of the evaluation absorption spectrum changes from a baseline of the reference absorption spectrum. When crystalline and amorphous particles are suspended in a liquid, the baseline of its absorption spectrum differs from the baseline of the absorption spectrum of the reference liquid. Therefore, whether or not there are crystalline and amorphous particles suspended in the liquid can be determined according to whether or not the baseline changes.

Preferably, ratios of crystalline and amorphous particles suspended in the liquid are determined according to the amount of change in the baseline of the evaluation absorption spectrum from the reference absorption spectrum. When crystalline and amorphous particles are suspended in the liquid, the baseline of its absorption spectrum changes depending on ratios of crystalline and amorphous particles in the liquid. Therefore, the ratios of crystalline and amorphous particles in the liquid can be determined according to the amount of change in the baseline.

Preferably, an amount of change in the baseline corresponding to a ratio of the crystalline particle is calculated beforehand, and the ratio of the amorphous particle is determined according to a difference between a total amount of change in the baseline and the amount of change in the baseline corresponding to the ratio of the crystalline particle. Subtracting the amount of change in the baseline caused by the crystalline particle from the total amount of change in the baseline can easily determine the ratio of the amorphous particle.

Preferably, a crystal form of the crystalline particle suspended in the liquid is determined according to a frequency of the absorption peak in the evaluation absorption spectrum. When a crystalline particle is suspended in a liquid, the frequency of an absorption peak of its absorption spectrum varies depending on the crystal form of the crystalline particle. Therefore, the crystal form of the crystalline particle suspended in the liquid can be determined according to the frequency of the absorption peak.

Preferably, when there are a plurality of absorption peaks in the evaluation absorption spectrum, respective ratios of crystal forms of crystalline particles suspended in the liquid are determined according to area ratios of the absorption peaks. When crystalline particles having different crystal forms are suspended in the liquid, its absorption spectrum has a plurality of absorption peaks, whose areas increase and decrease according to respective ratios of crystal forms of the crystalline particles in the liquid. Therefore, the respective ratios of crystal forms of the crystalline particles in the liquid can be determined according to the ratios of areas of absorption peaks.

Preferably, the liquid is mainly composed of water. In this case, the state of suspension of the drug can be evaluated in a particularly important liquid.

Preferably, a polymer is added to the liquid. This can inhibit the drug from being unevenly distributed over the surface of the liquid and uniformly suspend the drug in the liquid.

Preferably, a mixture of a polymer and the drug is added to the liquid. This can inhibit the drug from being unevenly distributed over the surface of the liquid and uniformly suspend the drug in the liquid.

The present invention also provides a drug evaluation device for evaluating crystallinity of a drug suspended in a liquid; the device comprising a light source for emitting laser light; a separating unit for separating the laser light emitted from the light source into pump light and probe light; a terahertz wave generator for generating a terahertz wave in response to the pump light incident thereon after being separated by the separating unit; an internal total reflection prism, having entrance and exit surfaces for the terahertz wave, for propagating therethrough the terahertz wave incident thereon from the entrance surface and totally reflecting the terahertz wave at a reflection surface so that the terahertz wave exits from the exit surface; a terahertz wave detector for receiving the terahertz wave emitted from the exit surface of the internal total reflection prism and the probe light separated by the separating unit and detecting a correlation between the terahertz wave and the probe light; a data acquiring unit, for acquiring an evaluation absorption spectrum for a frequency concerning the liquid arranged on the reflection surface of the internal total reflection prism, by an evanescent component of the terahertz occurring when the terahertz wave is totally reflected; and a data analyzer for determining whether or not there is a crystalline particle suspended in the liquid according to whether or not an absorption peak exists in the evaluation absorption spectrum acquired by the data acquiring unit.

This drug evaluation device obtains, by an attenuated reflection method using a terahertz wave, an evaluation absorption spectrum for a frequency with respect to a liquid to be evaluated. When a crystalline particle is suspended in a liquid, an absorption peak appears in its absorption spectrum. Therefore, whether or not there is a crystalline particle suspended in the liquid can be determined according to whether or not the absorption peak exists.

Preferably, the data analyzer determines the ratio of the crystalline particle suspended in the liquid according to the area of the absorption peak in the evaluation absorption spectrum. When the crystalline particle is suspended in the liquid, the area of the absorption peak in its absorption spectrum increases and decreases depending on the ratio of the crystalline particle in the liquid. Therefore, the ratio of the crystalline particle in the liquid can be determined according to the area of the absorption peak.

Preferably, the data analyzer has a reference absorption spectrum for a frequency concerning a liquid serving as a reference and determines whether or not there is an amorphous particle suspended in the liquid according to whether or not a baseline of the evaluation absorption spectrum changes from a baseline of the reference absorption spectrum. When an amorphous particle is suspended in a liquid, the baseline of its absorption spectrum differs from the baseline of the absorption spectrum of the reference liquid. Therefore, whether or not there is an amorphous particle suspended in the liquid can be determined according to whether or not the baseline changes.

Preferably, the data analyzer determines the ratio of the amorphous particle suspended in the liquid according to the amount of change in the baseline of the evaluation absorption spectrum from the baseline of the reference absorption spectrum. When the amorphous particle is suspended in a liquid, the baseline of its absorption spectrum varies according to the ratio of the amorphous particle in the liquid. Therefore, the ratio of the amorphous particle in the liquid can be determined according to the amount of change in the baseline.

Preferably, the data analyzer has a reference absorption spectrum for a frequency concerning a liquid serving as a reference and determines whether or not there are crystalline and amorphous particles suspended in the liquid according to whether or not a baseline of the evaluation absorption spectrum changes from a baseline of the reference absorption spectrum. When crystalline and amorphous particles are suspended in a liquid, the baseline of its absorption spectrum differs from the baseline of the absorption spectrum of the reference liquid. Therefore, whether or not there are crystalline and amorphous particles suspended in the liquid can be determined according to whether or not the baseline changes.

Preferably, the data analyzer determines ratios of crystalline and amorphous particles suspended in the liquid according to the amount of change in the baseline of the evaluation absorption spectrum from the reference absorption spectrum. When crystalline and amorphous particles are suspended in the liquid, the baseline of its absorption spectrum changes depending on ratios of crystalline and amorphous particles in the liquid. Therefore, the ratios of crystalline and amorphous particles in the liquid can be determined according to the amount of change in the baseline.

Preferably, the data analyzer has an amount of change in the baseline corresponding to a ratio of the crystalline particle beforehand and determines the ratio of the amorphous particle according to a difference between a total amount of change in the baseline and the amount of change in the baseline corresponding to the ratio of the crystalline particle. Subtracting the amount of change in the baseline caused by the crystalline particle from the total amount of change in the baseline can easily determine the ratio of the amorphous particle.

Preferably, the data analyzer determines a crystal form of the crystalline particle suspended in the liquid according to a frequency of the absorption peak in the evaluation absorption spectrum. When a crystalline particle is suspended in a liquid, the frequency of an absorption peak of its absorption spectrum varies depending on the crystal form of the crystalline particle. Therefore, the crystal form of the crystalline particle suspended in the liquid can be determined according to the frequency of the absorption peak.

Preferably, when there are a plurality of absorption peaks in the evaluation absorption spectrum, the data analyzer determines respective ratios of crystal forms of crystalline particles suspended in the liquid according to area ratios of the absorption peaks. When crystalline particles having different crystal forms are suspended in the liquid, its absorption spectrum has a plurality of absorption peaks, whose areas increase and decrease according to respective ratios of crystal forms of the crystalline particles in the liquid. Therefore, the respective ratios of crystal forms of the crystalline particles in the liquid can be determined according to the ratios of areas of absorption peaks.

The present invention makes it possible to evaluate drugs suspended in liquids.

DESCRIPTION OF THE PREFERRED EMBODIMENTS

In the following, preferred embodiments of the drug evaluation method and drug evaluation device in accordance with the present invention will be explained in detail with reference to the drawings.

Figure 1:
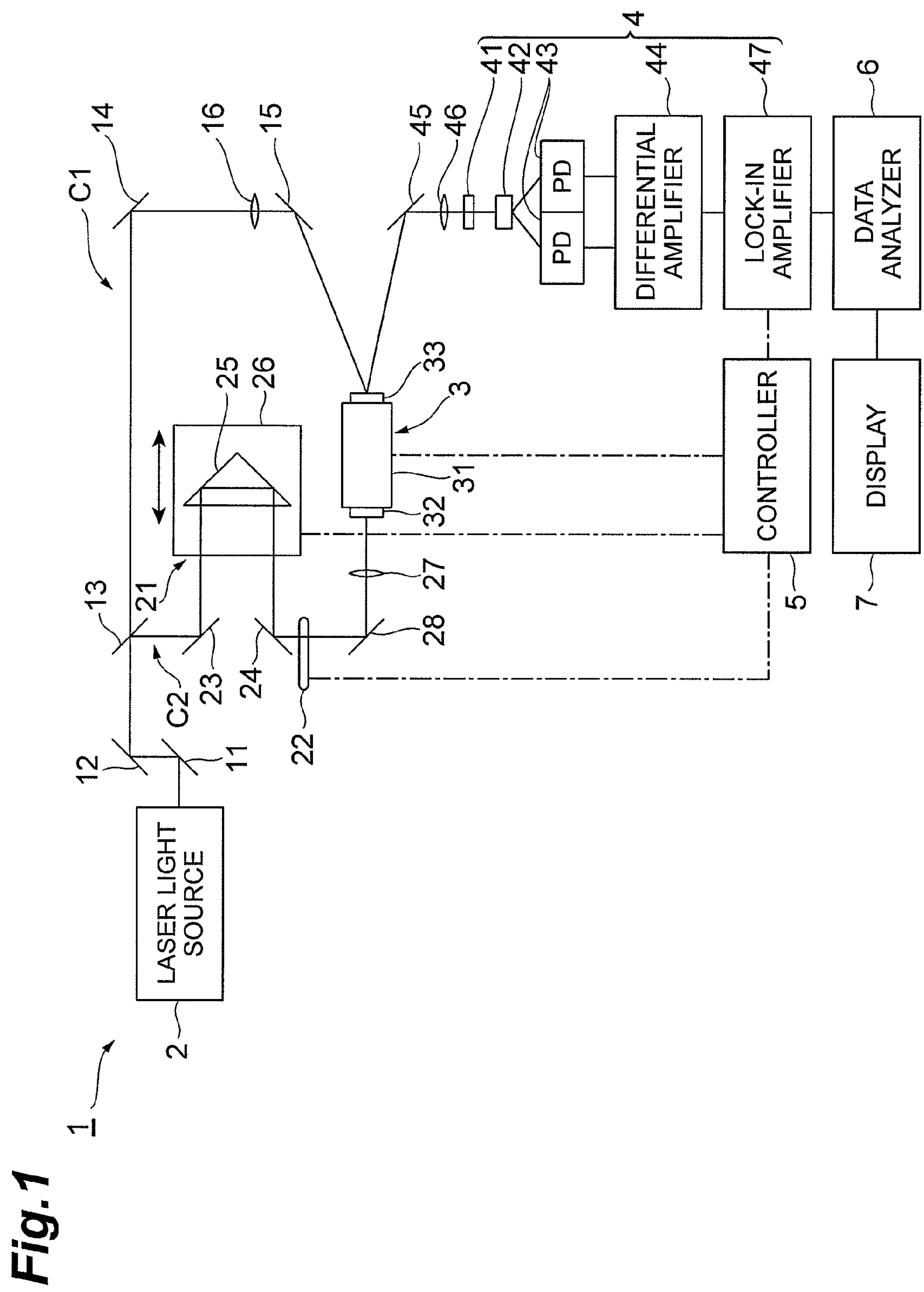
FIG. 1 is a diagram illustrating an embodiment of the drug evaluation device in accordance with the present invention.

FIG. 1 is a diagram illustrating an embodiment of the drug evaluation device in accordance with the present invention. As depicted, this drug evaluation device 1 comprises a laser light source 2 for emitting laser light; an integrated prism 3 in which a terahertz wave generating nonlinear optical crystal 32, an internal total reflection prism 31, and a terahertz wave detecting electro-optical crystal 33 are integrated; and a detector 4 for detecting a terahertz wave. The drug evaluation device 1 also comprises a controller 5 for controlling operations of the constituents mentioned above, a data analyzer 6 for analyzing data according to an output from the detector 4, and a display 7 for displaying results of processing in the data analyzer 6.

The laser light source 2 is a light source for generating a femtosecond pulsed laser. The laser light source 2 outputs a femtosecond pulsed laser having an average power of 120 mW and a repetition rate of 77 MHz, for example. The femtosecond pulsed laser emitted from the laser light source 2 is reflected by mirrors 11, 12 and then split by a beam splitter 13 into two, i.e., pump light 48 and probe light 49. A probe light optical path C1 through which the probe light 49 propagates is provided with mirrors 14, 15 and a lens 16, so that the probe light 49 is converged by the lens 16 and made incident on the terahertz wave detecting electro-optical crystal 33, which will be explained later.

On the other hand, a pump light optical path C2 through which the pump light 48 propagates is provided with a delay unit 21 and a modulator 22. The delay unit 21, which is constituted by a pair of mirrors 23, 24 and a reflecting prism 25 disposed on a movable stage 26, can regulate the delay of the pump light 48 by moving the position of the reflecting prism 25 back and forth with respect to the pair of mirrors 23, 24. The modulator 22 is a part which switches between transmission and shutoff of the pump light by a light chopper, for example. According to a signal from the controller 5, the modulator 22 modulates the transmission and shutoff of the pump light 48 at 1 kHz, for example.

Figure 2:
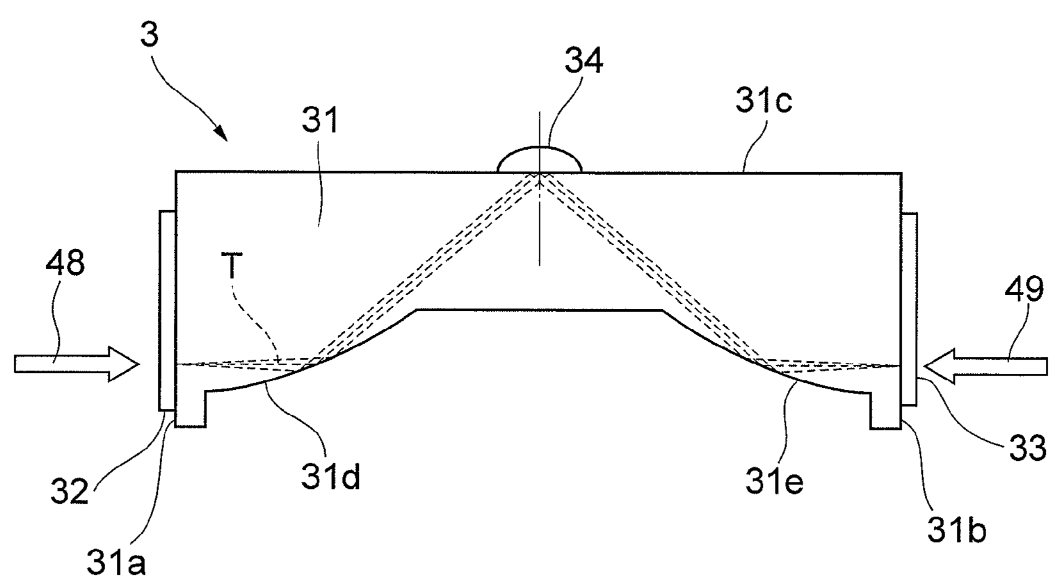
FIG. 2 is a diagram illustrating an example of integrated prisms constituting the drug evaluation device illustrated in FIG. 1.

The pump light 48 propagated through the pump light optical path C2 is reflected by a mirror 28 and then converged by a lens 27, so as to be made incident on the integrated prism 3. As illustrated in FIG. 2, the internal total reflection prism 31, which is formed by Si, for example, has an entrance surface 31*a* to which the terahertz wave generating nonlinear optical crystal 32 is integrally fixed and an exit surface 31*b* to which the terahertz wave detecting electro-optical crystal 33 is integrally fixed. The upper face of the internal total reflection prism 31 is a flat reflecting surface 31*c* on which an object to be measured 34 is mounted.

The object 34 in this embodiment is one suspending a drug which is hard to dissolve and easy to keep a crystal state in water, such as nifedipine and carbamazepine which are classified as poorly water soluble, for example, into a liquid mainly composed of water, such as deionized water, saline, and blood. When suspending the drug in the liquid, it is desirable that the drug and a polymer be mixed beforehand by using a mortar or the like such that the drug is uniformly suspended in the liquid. Examples of the polymer include amphiphilic polymers having hydrophilic and hydrophobic groups, such as poloxamers, polyethylene glycols, polyvinylpyrrolidone, polyvinyl alcohol, polyoxyethylene sorbitan fatty acid esters, polyoxyethylene stearate, polyoxyethylene alkyl ethers, polylactic acid, aminoalkyl methacrylate copolymers, and methacrylic acid copolymers. Other examples of the liquid include ethanol, methanol, acetone, ethyl acetate, isopropanol, dioxane, dimethyl sulfoxide, dimethyl formamide, formamide, formic acid, acetic acid, butyric acid, trifluoroacetic acid, hydrochloric acid, sulfuric acid, and nitric acid.

As illustrated in FIG. 2, a first optical surface 31*d* for turning a terahertz wave T generated in the terahertz wave generating nonlinear optical crystal 32 into parallel light directed to the reflecting surface 31*c* is disposed on the bottom face of the internal total reflection prism 31 between the entrance surface 31*a* and reflecting surface 31*c*. A second optical surface 31*e* for converging the terahertz wave T totally reflected by the reflecting surface 31*c* onto the exit surface 31*b* is disposed between the reflecting surface 31*c* and exit surface 31*b*. The first and second optical surfaces 31*d*, 31*e* are formed by processing the bottom face of the internal total reflection prism 31 into a predetermined shape.

For example, ZnTe can be used as the terahertz wave generating nonlinear optical crystal 32 and terahertz wave detecting nonlinear electro-optical crystal 33. The terahertz wave T generated from such an element has a pulse on the order of several picoseconds in general. When the pump light 48 is incident on the terahertz wave generating optical crystal 32, the pump light 48 is converted into the terahertz wave T by the optical rectification effect of the nonlinear optical crystal. When the terahertz wave T and probe light 49 are incident on the terahertz wave detecting nonlinear electro-optical crystal 33 at the same time, the probe light 49 experiences birefringence caused by the Pockels effect of the electro-optical crystal. The amount of birefringence of the probe light 49 is proportional to the electric field intensity of the terahertz wave T. Therefore, the terahertz wave T can be detected from the amount of birefringence of the probe light 49.

As illustrated in FIG. 1, the detector 4 for detecting the terahertz wave is constituted by a quarter-wave plate 41, a polarizer 42, a pair of photodiodes 43, 43, a differential amplifier 44, and a lock-in amplifier 47, for example. The probe light 49 reflected by the terahertz wave detecting electro-optical crystal 33 is guided to the detector 4 by a mirror 45, converged by a lens 46, passed through the quarter-wave plate 41, and then separated by the polarizer 42 such as a Wollaston prism into vertical and horizontal linearly-polarized components. The vertical and horizontal linearly-polarized components of the probe light 49 are converted into respective electric signals by the pair of photodiodes 43, 43, while their difference is detected by the differential amplifier 44. An output signal from the differential amplifier 44 is amplified by the lock-in amplifier 47 and then fed into the data analyzer 6.

When the terahertz wave T and probe light 49 are incident on the terahertz wave detecting electro-optical crystal 33 at the same time, the differential amplifier 44 outputs a signal having an intensity proportional to the electric field intensity of the terahertz wave T; otherwise, the differential amplifier 44 outputs no signal. Evanescent waves emitted when the terahertz wave T is reflected by the reflecting surface 31*c* of the internal total reflection prism 31 interact with the object 34 mounted on the reflecting surface 31*c* of the internal total reflection prism 31, whereby the reflectance of the terahertz wave T changes from that in the case where the object 34 is not mounted. Therefore, a spectral characteristic (absorption coefficient with respect to frequency here) of the object 34 can be obtained by measuring the change in reflectance of the terahertz wave T.

The data analyzer 6 is a part corresponding to the data acquiring unit and data analyzer in the present invention. Physically, the data analyzer 6 is a computer system having a CPU (central processing unit), a memory, an input device, the display 7, and the like. According to a signal fed from the lock-in amplifier 47, the data analyzer 6 executes a dedicated analysis program, so as to cause the display 7 to display results of evaluation of the suspended state of the drug in the liquid concerning the object 34.

Figure 3:
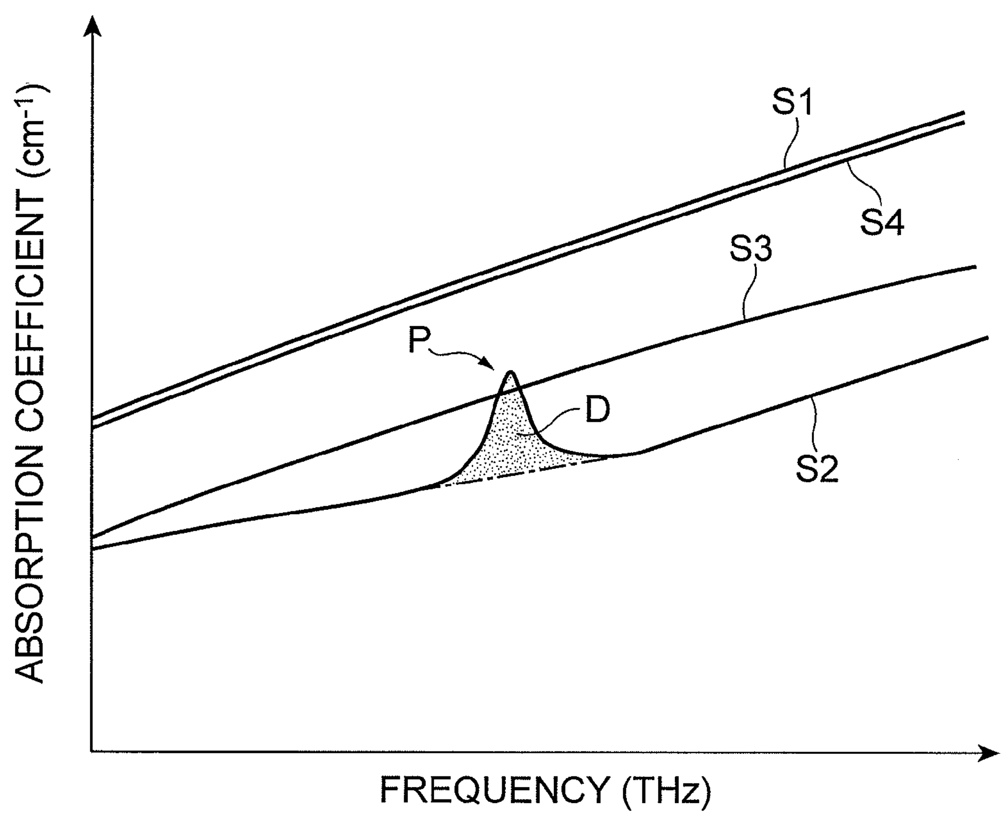
FIG. 3 is a schematic chart of spectral patterns of absorption spectra for suspended states of drugs in liquids.

The knowledge in the data analysis method by the data analyzer 6 will now be explained in detail. The state of the drug in the liquid is mainly classified into three states of being (A) suspended as crystalline particles, (B) suspended as amorphous particles, and (C) dissolved into molecules. For such states, FIG. 3 illustrates a schematic chart of respective spectral patterns of absorption spectra with respect to frequency concerning liquids to be evaluated by an attenuated reflection method using the terahertz wave as mentioned above. This chart is an example of illustrating how the absorption spectrum of a liquid in which particles are suspended changes from an absorption spectrum of a reference liquid.

While using deionized water as a reference liquid, this chart illustrates the absorption spectrum of the reference liquid, that of a liquid in which crystalline particles are suspended, that of a liquid in which amorphous particles are suspended, and that of a liquid containing dissolved molecules as S1, S2, S3, and S4, respectively. Here, the liquid, suspended drug, and employed polymer are deionized water, nifedipine, and poloxamer 188, respectively.

As illustrated in FIG. 3, no absorption peak exists in the absorption spectrum S1 of deionized water, and its baseline (a line approximating the absorption spectrum) is located at the highest position. In the absorption spectrum S2 of the liquid in which crystalline particles are suspended, on the other hand, an absorption peak P appears at a predetermined frequency, and its baseline lowers greatly from that of the absorption spectrum S1.

Unlike in the absorption spectrum S2, no absorption peak appears in the absorption spectrum S3 in which amorphous particles are suspended, and its baseline lowers less than that of the absorption spectrum S2 does. The absorption spectrum S4 of the liquid containing dissolved molecules is substantially the same as the absorption spectrum S1 of deionized water and has no peak, and its baseline changes negligibly, if any, from that of the absorption spectrum S1.

Example 1

Measurement of Nifedipine Suspension

Figure 4:
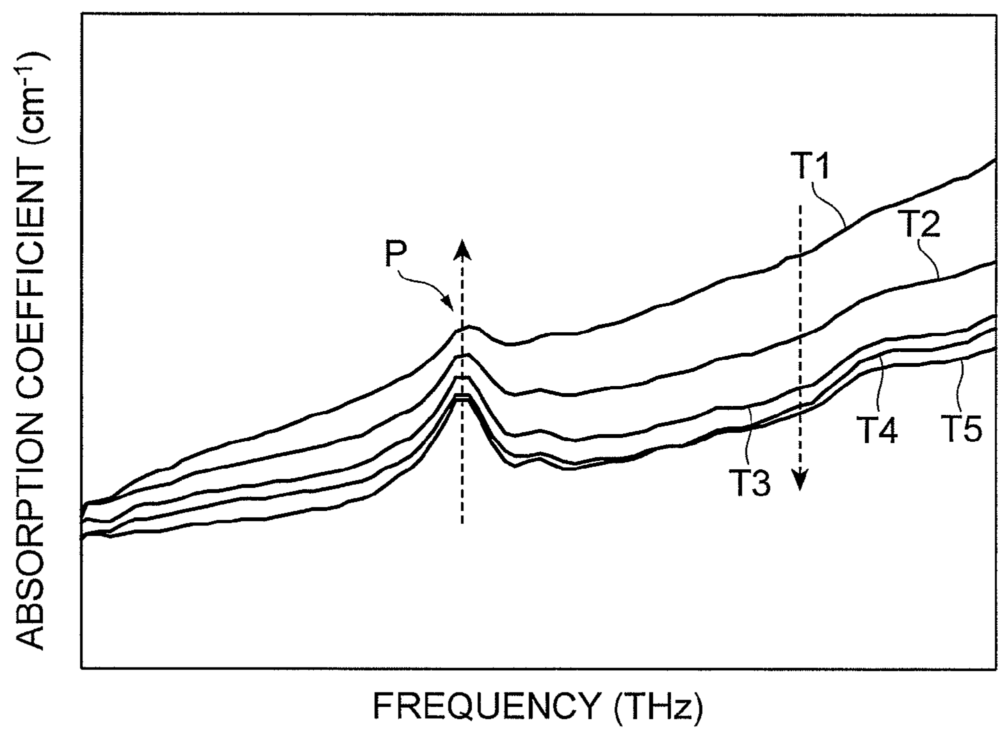
FIG. 4 is a chart illustrating results of actually measuring tendencies in absorption spectra in a case where the ratio of crystalline particles in a liquid varies.

FIG. 4 illustrates results of actually measuring absorption spectra in a case where the ratio of crystalline particles in a liquid varies. This chart successively illustrates absorption spectra T1 to T5 in the case where the ratio of crystalline particles in the liquid gradually increases. Here, the liquid, suspended drug, and employed polymer are deionized water, nifedipine, and poloxamer 188, respectively. As the ratio of crystalline particles increases, as illustrated in FIG. 4, the absorption peak P rises, and the peak area D (the area of the part defined by the line approximating the part excluding the absorption peak and the absorption peak; see FIG. 3) increases. The baseline lowers at a fixed rate in the absorption spectra T1 to T5. That is, the absorption coefficient decreases.

Figure 5:
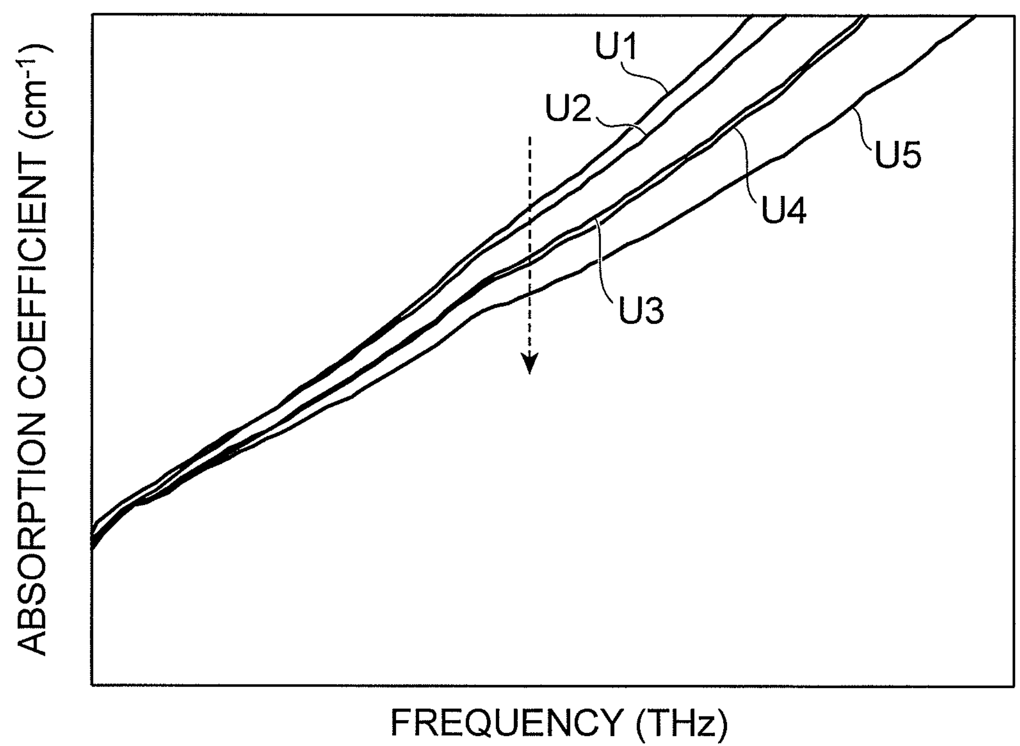
FIG. 5 is a chart illustrating results of actually measuring tendencies in absorption spectra in a case where the ratio of amorphous particles in a liquid varies.

FIG. 5 illustrates results of actually measuring absorption spectra in a case where the ratio of amorphous particles in a liquid varies. This chart successively illustrates absorption spectra U1 to U5 in the case where the ratio of crystalline particles in the liquid gradually increases. Here, the liquid, suspended drug, and employed polymer are deionized water, nifedipine, and poloxamer 188, respectively. As the ratio of amorphous particles increases, as illustrated in FIG. 5, the baseline gradually lowers in the absorption spectra U1 to U5 at a rate smaller than that in the case of FIG. 4.

The results of FIGS. 4 and 5 conclude that (a) the peak area of the absorption spectrum increases in proportion to the ratio of crystalline particles suspended in the liquid, (b) the amount by which the baseline of the absorption peak lowers is in proportion to the ratio of particles (which may be either crystalline or amorphous) suspended in the liquid, while the extent of lowering varies between the crystalline and amorphous particles, and (c) the ratio of dissolved molecules does not affect the peak area and baseline.

Figure 6:
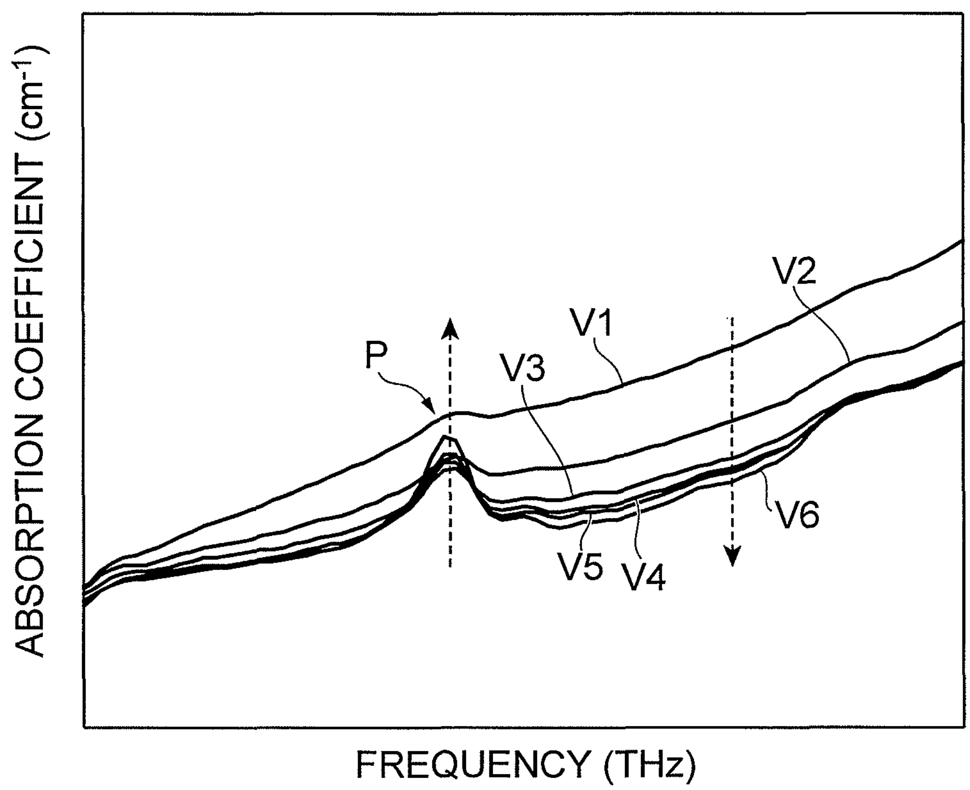
FIG. 6 is a chart illustrating results of actually measuring tendencies in absorption spectra in a case where crystalline and amorphous particles are suspended as a mixture in a liquid.

FIG. 6 illustrates results of actually measuring absorption spectra in a case where crystalline and amorphous particles are suspended as a mixture in a liquid. This chart illustrates an absorption spectrum in which small amount of crystalline and large amount of amorphous particles respectively are suspended in a liquid as V1 and, in sequence, absorption spectra V2 to V6 in the case of gradually increasing crystalline particles and decreasing amorphous particles, respectively, with respect to V1. Here, the liquid, suspended drug, and employed polymer are deionized water, nifedipine, and poloxamer 188, respectively.

In the case where crystalline and amorphous particles are suspended as a mixture in a liquid, the peak area of the absorption spectrum and the lowering amount of its baseline change according to their mix ratio as illustrated in FIG. 6. These results conclude that the change in absorption spectrum according to the ratio of crystalline particles and the change in absorption spectrum according to the ratio of amorphous particles occur independently from each other.

According to such knowledge, the data analyzer 6 determines whether or not and by what ratios crystalline and amorphous particles exist in the object 34. More specifically, the data analyzer 6 has beforehand an absorption spectrum of a reference liquid (reference absorption spectrum), an absorption spectrum of a drug to be evaluated as being suspended in a liquid for each kind of liquid, a calibration curve I in which the area of the absorption peak and the amount of suspension of crystalline particles are related with each other, a calibration curve II in which the lowering amount of the baseline at a predetermined frequency and the amount of suspension of crystalline particles are related with each other, and a calibration curve III in which the lowering amount of the baseline at a predetermined frequency and the amount of suspension of amorphous particles are related with each other.

When a total amount of 23 mg/ml of a drug A is suspended in a liquid, for example, the data analyzer 6 initially determines whether or not an absorption peak appears at a predetermined frequency (e.g., 1.2 THz) of its absorption spectrum (evaluation absorption spectrum). When no absorption peak appears, the data analyzer 6 determines that no crystalline particles are suspended in the liquid. When the peak appears, on the other hand, the data analyzer 6 obtains its peak area and calculates the amount of suspension of crystalline particles by using the calibration curve I.

Assuming that the amount of suspension of crystalline particles is 8.5 mg/ml, for example, the data analyzer 6 subsequently obtains the amount by which the baseline lowers from the reference absorption spectrum at a predetermined frequency (e.g., 0.75 THz). When the lowering amount of the baseline is 26 $cm^{-1}$ while the lowering amount of the baseline caused by 8.5 mg/ml of crystalline particles obtained from the calibration curve II is 17 $cm^{-1}$ here, the lowering amount of 9 $cm^{-1}$ as the difference derives from amorphous particles. Using the calibration curve III, the data analyzer 6 calculates the amount of suspension of amorphous particles. When the amount of suspension of amorphous particles is 12 mg/ml here, for example, while the total amount of the drug A is 23 mg/ml, the data analyzer 26 determines that the remaining 2.5 mg/ml of the drug A has dissolved as molecules.

Example 2

Measurement of Carbamazepine Suspension

Figure 7:
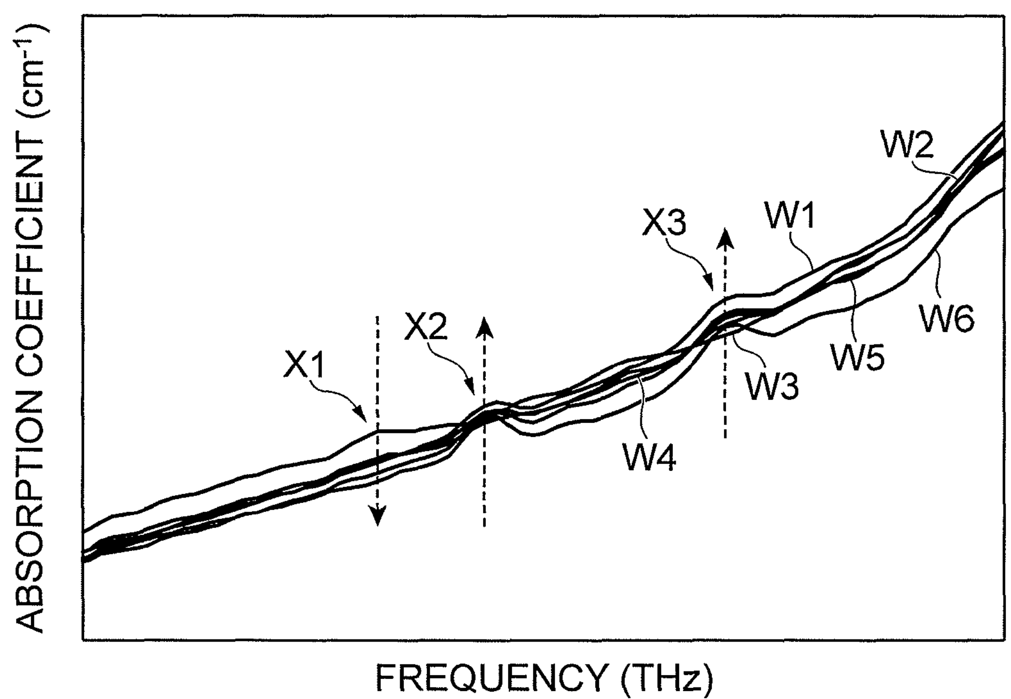
FIG. 7 is a chart illustrating results of actually measuring tendencies in absorption spectra in a case where crystalline particles having different crystal forms are suspended in a liquid.

FIG. 7 illustrates results of actually measuring absorption spectra in a case where crystalline particles having different crystal forms are suspended in a liquid. While I- and III-type crystals of carbamazepine are suspended in deionized water, for example, FIG. 7 illustrates an absorption spectrum W1 in which large amount of the I-type crystal of carbamazepine and small amount of the III-type crystal of carbamazepine are suspended and, in sequence, absorption spectra W2 to W5 in the case of gradually increasing III-type crystal of carbamazepine and decreasing I-type crystal of carbamazepine, respectively, with respect to W1.

When crystalline particles having different crystal forms are suspended, absorption peaks appear at different frequencies according to the crystal forms of crystalline particles as illustrated in FIG. 7. Here, an absorption peak X1 appears according to the I-type crystal of carbamazepine, while two absorption peaks X2, X3 appear according to the III-type crystal of carbamazepine. The peak area increases and decreases among the absorption peaks X1 to X3 according to the ratios of I- and III-type crystals of carbamazepine in the liquid. Based on such knowledge, when a plurality of absorption peaks appear in the absorption spectrum, the data analyzer 6 determines the ratios of crystalline particles in the liquid for the respective crystal forms according to the area ratios of absorption peaks X1 to X3.

As explained in the foregoing, the drug evaluation device 1 obtains an evaluation absorption spectrum for a frequency concerning the liquid to be evaluated according to an attenuated reflection method using a terahertz wave. When crystalline particles are suspended in a liquid, an absorption peak having a peak area corresponding to the amount of suspension appears in its absorption spectrum. Therefore, whether or not and by what ratio crystalline particles are suspended in the liquid can be determined according to whether or not absorption peaks exist and the peak areas.

When amorphous particles are suspended in a liquid, the baseline of its absorption spectrum lowers according to the ratio of amorphous particles in the liquid. Therefore, whether or not and by what ratio amorphous particles exist in the liquid can be determined according to the lowering amount of the baseline.

When a plurality of crystalline particles having different crystal forms are suspended in a liquid, its absorption spectrum has a plurality of absorption peaks, whose areas increase and decrease according to respective ratios of crystal forms of the crystalline particles in the liquid. Therefore, the respective ratios of crystal forms of the crystalline particles in the liquid can be determined according to the ratios of areas of absorption peaks.

What is claimed is:

1. A drug evaluation method for evaluating crystallinity of a drug suspended in a liquid, the method comprising:
- obtaining by an attenuated reflection method using a terahertz wave an evaluation absorption spectrum for a frequency concerning the liquid to be evaluated; and
- determining whether or not there is a crystalline particle suspended in the liquid according to whether or not an absorption peak exists in the evaluation absorption spectrum,
- wherein a ratio of the crystalline particle suspended in the liquid is determined according to the area of the absorption peak in the evaluation absorption spectrum.

2. A drug evaluation method according to claim 1, wherein the liquid is mainly composed of water.

3. A drug evaluation method according to claim 1, wherein a polymer is added to the liquid.

4. A drug evaluation method according to claim 1, wherein a mixture of a polymer and the drug is added to the liquid.

5. A drug evaluation method for evaluating crystallinity of a drug suspended in a liquid, the method comprising:
- obtaining by an attenuated reflection method using a terahertz wave an evaluation absorption spectrum for a frequency concerning the liquid to be evaluated; and
- determining whether or not there is a crystalline particle suspended in the liquid according to whether or not an absorption peak exists in the evaluation absorption spectrum,
- wherein a reference absorption spectrum for a frequency concerning a liquid serving as a reference is obtained by an attenuated reflection method using a terahertz wave; and
- wherein whether or not there is an amorphous particle suspended in the liquid is determined according to whether or not a baseline of the evaluation absorption spectrum changes from a baseline of the reference absorption spectrum.

6. A drug evaluation method according to claim 5, wherein a ratio of the amorphous particle suspended in the liquid is determined according to the amount of change in the baseline of the evaluation absorption spectrum from the baseline of the reference absorption spectrum.

7. A drug evaluation method according to claim 5, wherein the liquid is mainly composed of water.

8. A drug evaluation method according to claim 5, wherein a polymer is added to the liquid.

9. A drug evaluation method according to claim 5, wherein a mixture of a polymer and the drug is added to the liquid.

10. A drug evaluation method for evaluating crystallinity of a drug suspended in a liquid, the method comprising:

obtaining by an attenuated reflection method using a terahertz wave an evaluation absorption spectrum for a frequency concerning the liquid to be evaluated; and determining whether or not there is a crystalline particle suspended in the liquid according to whether or not an absorption peak exists in the evaluation absorption spectrum, wherein a reference absorption spectrum for a frequency concerning a liquid serving as a reference is obtained by an attenuated reflection method using a terahertz wave; and wherein whether or not there are crystalline and amorphous particles suspended in the liquid is determined according to whether or not a baseline of the evaluation absorption spectrum changes from a baseline of the reference absorption spectrum.

11. A drug evaluation method according to claim 10, wherein ratios of crystalline and amorphous particles suspended in the liquid are determined according to the amount of change in the baseline of the evaluation absorption spectrum from the reference absorption spectrum.

12. A drug evaluation method according to claim 11, wherein an amount of change m the baseline corresponding to a ratio of the crystalline particle is calculated beforehand, and the ratio of the amorphous particle is determined according to a difference between a total amount of change in the baseline and the amount of change in the baseline corresponding to the ratio of the crystalline particle.

13. A drug evaluation method according to claim 10, wherein the liquid is mainly composed of water.

14. A drug evaluation method according to claim 10, wherein a polymer is added to the liquid.

15. A drug evaluation method according to claim 10, wherein a mixture of a polymer and the drug is added to the liquid.

16. A drug evaluation method for evaluating crystallinity of a drug suspended in a liquid, the method comprising:

obtaining by an attenuated reflection method using a terahertz wave an evaluation absorption spectrum for a frequency concerning the liquid to be evaluated; and determining whether or not there is a crystalline particle suspended in the liquid according to whether or not an absorption peak exists in the evaluation absorption spectrum, wherein a crystal form of the crystalline particle suspended in the liquid is determined according to a frequency of the absorption peak in the evaluation absorption spectrum.

17. A drug evaluation method according to claim 16, wherein, when there are a plurality of absorption peaks in the evaluation absorption spectrum, respective ratios of crystal forms of crystalline particles suspended in the liquid are determined according to area ratios of the absorption peaks.

18. A drug evaluation method according to claim 16, wherein the liquid is mainly composed of water.

19. A drug evaluation method according to claim 16, wherein a polymer is added to the liquid.

20. A drug evaluation method according to claim 16, wherein a mixture of a polymer and the drug is added to the liquid.

21. A drug evaluation device for evaluating crystallinity of a drug suspended in a liquid, the device comprising:

a light source for emitting laser light;

a separating unit for separating the laser light emitted from the light source into puma light and probe light;

a terahertz wave generator for generating a terahertz wave in response to the pump light incident thereon after being separated by the separating unit;

an internal total reflection prism, having entrance and exit surfaces for the terahertz wave, for propagating therethrough the terahertz wave incident thereon from the entrance surface and totally reflecting the terahertz wave at a reflection surface so that the terahertz wave exits from the exit surface;

a terahertz wave detector for receiving the terahertz wave emitted from the exit surface of the internal total reflection prism and the probe light separated by the separating unit and detecting a correlation between the terahertz wave and the probe light;

a data acquiring unit, for acquiring an evaluation absorption spectrum for a frequency concerning the liquid arranged on the reflection surface of the internal total reflection prism, by an evanescent component of the terahertz occurring when the terahertz wave is totally reflected; and a data analyzer for determining whether or not there is a crystalline particle suspended in the liquid according to whether or not an absorption peak exists in the evaluation absorption spectrum acquired by the data acquiring unit, wherein the data analyzer determines a ratio of the crystalline particle suspended in the liquid according to the area of the absorption peak in the evaluation absorption spectrum.

22. A drug evaluation device for evaluating crystallinity of a drug suspended in a liquid, the device comprising:

a light source for emitting laser light;

a separating unit for separating the laser light emitted from the light source into pump light and probe light;

a terahertz wave generator for generating a terahertz wave in response to the pump light incident thereon after being separated by the separating unit;

an internal total reflection prism, having entrance and exit surfaces for the terahertz wave, for propagating therethrough the terahertz wave incident thereon from the entrance surface and totally reflecting the terahertz wave at a reflection surface so that the terahertz wave exits from the exit surface;

a terahertz wave detector for receiving the terahertz wave emitted from the exit surface of the internal total reflection prism and the probe light separated by the separating unit and detecting a correlation between the terahertz wave and the probe light;

a data acquiring unit, for acquiring an evaluation absorption spectrum for a frequency concerning the liquid arranged on the reflection surface of the internal total reflection prism, by an evanescent component of the terahertz occurring when the terahertz wave is totally reflected; and a data analyzer for determining whether or not there is a crystalline article suspended in the liquid according to whether or not an absorption peak exists in the evaluation absorption spectrum acquired by the data acquiring unit, wherein the data analyzer has a reference absorption spectrum for a frequency concerning a liquid serving as a reference and determines whether or not there is an amorphous particle suspended in the liquid according to whether or not a baseline of the evaluation absorption spectrum changes from a baseline of the reference absorption spectrum.

23. A drug evaluation device according to claim 22, wherein the data analyzer determines the ratio of the amorphous particle suspended in the liquid according to the amount of change in the baseline of the evaluation absorption spectrum from the baseline of the reference absorption spectrum.

24. A drug evaluation device for evaluating crystallinity of a drug suspended in a liquid, the device comprising:

a light source for emitting laser light;

a separating unit for separating the laser light emitted from the light source into pump light and probe light;

a terahertz wave generator for generating a terahertz wave in response to the pump light incident thereon after being separated by the separating unit;

an internal total reflection prism, having entrance and exit surfaces for the terahertz wave, for propagating therethrough the terahertz wave incident thereon from the entrance surface and totally reflecting the terahertz wave at a reflection surface so that the terahertz wave exits from the exit surface;

a terahertz wave detector for receiving the terahertz wave emitted from the exit surface of the internal total reflection prism and the probe light separated by the separating unit and detecting a correlation between the terahertz wave and the probe light;

a data acquiring unit, for acquiring an evaluation absorption spectrum for a frequency concerning the liquid arranged on the reflection surface of the internal total reflection prism, by an evanescent component of the terahertz occurring when the terahertz wave is totally reflected; and a data analyzer for determining whether or not there is a crystalline particle suspended in the liquid according to whether or not an absorption peak exists in the evaluation absorption spectrum acquired by the data acquiring unit, wherein the data analyzer has a reference absorption spectrum for a frequency concerning a liquid serving as a reference and determines whether or not there is an amorphous particle suspended in the liquid according to whether or not a baseline of the evaluation absorption spectrum changes from a baseline of the reference absorption spectrum.

25. A drug evaluation device according to claim 24, wherein the data analyzer determines ratios of crystalline and amorphous particles suspended in the liquid according to the amount of change in the baseline of the evaluation absorption spectrum from the reference absorption spectrum.

26. A drug evaluation device according to claim 25, wherein the data analyzer has an amount of change in the baseline corresponding to a ratio of the crystalline particle beforehand and determines the ratio of the amorphous particle according to a difference between a total amount of change in the baseline and the amount of change in the baseline corresponding to the ratio of the crystalline particle.

27. A drug evaluation device for evaluating crystallinity of a drug suspended in a liquid, the device comprising:

a light source for emitting laser light;

a separating unit for separating the laser light emitted from the light source into pump light and probe light;

a terahertz wave generator for generating a terahertz wave in response to the pump light incident thereon after being separated by the separating unit;

an internal total reflection prism, having entrance and exit surfaces for the terahertz wave, for propagating therethrough the terahertz wave incident thereon from the entrance surface and totally reflecting the terahertz wave at a reflection surface so that the terahertz wave exits from the exit surface;

a terahertz wave detector for receiving the terahertz wave emitted from the exit surface of the internal total reflection prism and the probe light separated by the separating unit and detecting a correlation between the terahertz wave and the probe light;

a data acquiring unit, for acquiring an evaluation absorption spectrum for a frequency concerning the liquid arranged on the reflection surface of the internal total reflection prism, by an evanescent component of the terahertz occurring when the terahertz wave is totally reflected; and a data analyzer for determining whether or not there is a crystalline particle suspended in the liquid according to whether or not an absorption peak exists in the evaluation absorption spectrum acquired by the data acquiring unit, wherein the data analyzer determines a crystal form of the crystalline particle suspended in the liquid according to a frequency of the absorption peak in the evaluation absorption spectrum.

28. A drug evaluation device according to claim 27, wherein, when there are a plurality of absorption peaks in the evaluation absorption spectrum, the data analyzer determines respective ratios of crystal forms of crystalline particles suspended in the liquid according to area ratios of the absorption peaks.

* * * * *